United States Patent [19]

Gavlak et al.

[11] Patent Number: 5,214,412

[45] Date of Patent: May 25, 1993

[54] LEAK DETECTOR METHOD ESTABLISHING TWO DIFFERENT THRESHOLD LEVELS

[75] Inventors: Michael A. Gavlak, Buffalo, N.Y.; Brian G. Wicke, Bloomfield Hills, Mich.

[73] Assignee: General Motors Corporation, Detroit, Mich.

[21] Appl. No.: 801,192

[22] Filed: Dec. 2, 1991

[51] Int. Cl.$^5$ ............................................. G08B 17/10
[52] U.S. Cl. .................................. 340/632; 340/605; 324/455; 73/23.21; 73/40.5 R
[58] Field of Search ............... 340/632, 633, 634, 605; 73/23.2, 23.21, 40, 40.5, 31.02; 324/455

[56] References Cited

U.S. PATENT DOCUMENTS

| | | | |
|---|---|---|---|
| 3,076,139 | 1/1963 | Roberts | 73/40.7 |
| 3,786,675 | 1/1974 | Delatorre et al. | 340/632 |
| 4,282,521 | 8/1981 | Lieberman | 340/632 |
| 4,488,118 | 12/1984 | Jeffers et al. | 340/632 |
| 4,797,621 | 1/1989 | Anderson et al. | 340/605 |
| 4,879,546 | 11/1989 | Dunham et al. | 340/632 |

*Primary Examiner*—Jin F. Ng
*Assistant Examiner*—Jeffery A. Hofsass
*Attorney, Agent, or Firm*—Ronald L. Phillips

[57] ABSTRACT

A leak detector has a dual sensitivity due to two thresholds, a first established by a standard leak of the test gas representing the smallest leak to be detected, and the second as a fraction of the first one. A variable autozero level is used to compensate for background but is limited in its range to prevent masking of the leak by the autozero level. When measured gas concentration in excess of the autozero level exceeds the second threshold, the autozero value is held at a fixed value and an annuciator produces a signal as a function of the concentration so that the maximum concentration and the leak site can be found. When the leak site is found, the operator selects the first threshold for comparison with the gas concentration in excess of the held autozero value to determine whether the leak exceeds the rejection level.

9 Claims, 3 Drawing Sheets

LEAK DETECTOR METHOD ESTABLISHING TWO DIFFERENT THRESHOLD LEVELS

FIELD OF THE INVENTION

This invention relates to the detection of gaseous leaks into the atmosphere and particularly to a method of detecting such leaks.

BACKGROUND OF THE INVENTION

In the manufacture of refrigeration systems containing a gaseous refrigerant it is necessary to monitor the equipment for leaks. Since it is desired that the systems be used for years without replenishment of refrigerant, small leaks should be detected and repaired. It is customary to establish a limit leak value, such as 0.4 ounces per year, and to ignore smaller leaks and detect and repair larger leaks.

Detecting the absolute value of gas concentration near a suspected leak location can give misleading results. Because the room in which testing takes place may have significant background levels of the test gas, it has become a common practice to detect the background level and subtract it from the measured concentration to indicate the levels above background. Further, it is known to frequently update the background level during leak detection to accommodate changes in the background. This method, called autozeroing, is subject to error when the detector is held near a leak long enough for the leak itself to contribute to the measured background, thereby greatly reducing sensitivity of the device.

An autozeroing arrangement is disclosed, for example, in the U.S. Pat. No. 3,786,675 to Delatorre et al which uses a gas detector which is subject to considerable temperature drift. Autozeroing is used to null the detector output to cancel out the temperature drift as well as the background. The patent proposes to hold the autozero value in memory for 12 seconds once a certain output is reached to allow measurements above the memory value. After that time, or upon actuating a switch, the circuit is again zeroed to cancel out background gas and reduce the effects of temperature drift. This approach could mask serious detector drift problems or sensitivity changes which should come to the attention of the operator, and would also reduce sensitivity by cancelling out gas readings due to a leak in addition to actual background gas.

SUMMARY OF THE INVENTION

It is therefore an object of the invention to provide a method of leak detection which is more sensitive than previous methods, and which has improved autozeroing that is not apt to mask detector drift or to reduce sensitivity by masking the leak.

The invention is carried out by the method of detecting leaks using a leak detector for measuring the concentration of a test gas and having a probe, an annunciator, and a switch, comprising the steps of: establishing a limit value of gas concentration; establishing a threshold lower than the limit value to provide increased sensitivity to low concentrations; moving the probe along a path and continuously measuring background level and the gas concentration from leaks; when the gas concentration exceeds the threshold, indicating changes in the concentration; in response to the indicated changes, moving the probe to seek the maximum concentration; when the probe is near the maximum concentration, comparing the gas concentration to the limit value; and issuing a signal when the concentration exceeds the limit value.

BRIEF DESCRIPTION OF THE DRAWINGS

The above and other advantages of the invention will become more apparent from the following description taken in conjunction with the accompanying drawings wherein like references refer to like parts and wherein.

DESCRIPTION OF THE INVENTION

The ensuing description is directed to a method or algorithm for operation of a leak detector which is applicable to any of several commercially available detectors, preferably those having a microprocessor based circuit and adapted for programming to carry out portions of the algorithm. The method or algorithm is a hybrid, involving interactive procedures practiced by the operator as well as functions programmed into the detectors. Thus a particular detector is not part of the invention and is not described herein. Although the method was developed specifically for detecting leaks of refrigerant gas, the application of the concepts are not so limited.

In general leak detectors pass sampled gas through an electrical detector element which outputs a signal. When the gas being searched for, called the test gas, enters the element, the signal changes in proportion to the concentration of the test gas. Signal conditioning usually involves autozeroing to obtain a measure of background levels of test gas and to cancel out the typical output of the signal in the absence of a leak. The autozeroing traditionally comprises, for example an R-C circuit or the equivalent with about a 10 second time constant to determine an updated average of recent signals. When moving the detector near a leak a dramatic change in signal level takes place and if the signal level less the autozero value reaches a threshold level it triggers a leak alarm comprising a flashing light with frequency proportional to the magnitude of the leak or an audible alarm having a pitch proportional to the leak. However, if the concentration of sensed gas is high for several seconds, the autozero value increases to cancel much of the signal and the leak can appear to be much smaller than it actually is. Consequently, a reduction in apparent sensitivity results, often by a factor of 5 or 10 when a reasonable leak scan rate of about two inches per second is used.

According to the enhanced algorithm of this invention two thresholds are used: a calibrated "pass/fail" level which is similar to that used in prior detectors, and a much lower "search" threshold to provide high search sensitivity. When the measurement signal less the autozero value (or "difference" signal) is below the search threshold the autozero value is restrained to a limited range so that it does not mask low gas levels due to leaks. When the difference signal is above the search threshold, the autozero is not allowed to change at all, thereby preventing understated indications of the leak when the leak is being pin-pointed and compared to the pass/fail level.

Figure 1:
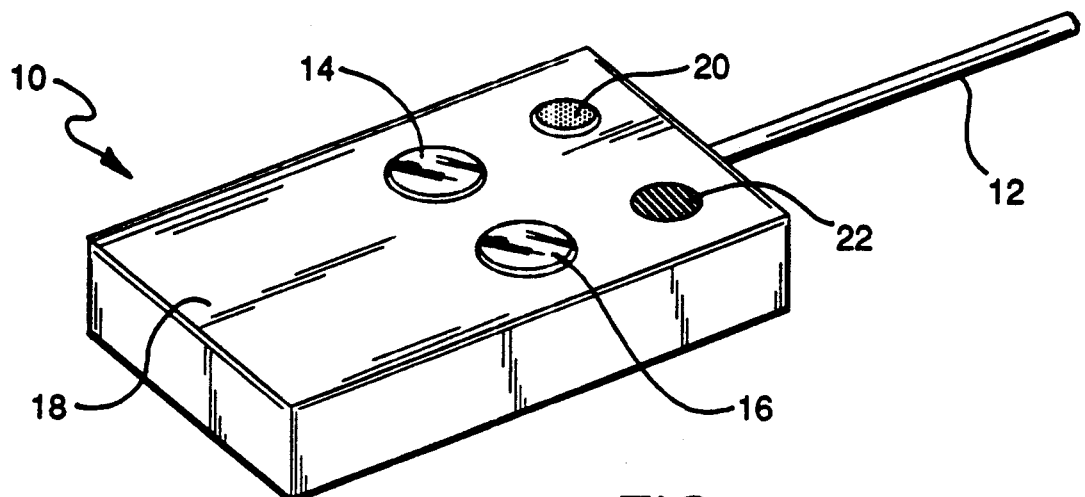
FIG. 1 is a schematic view of a leak detector used to practice the method of the invention.

FIG. 1 illustrates a typical hand-held leak detector 10 having a probe 12 which is moved over the inspection region. A calibration switch operated by a pushbutton 14 and a sensitivity switch operated by a pushbutton 16 are mounted on the panel 18 of the detector 10. An annunciator such as an LED or other light 20 and/or an alarm 22 on the panel 18 provide warning and alarm signals.

Figure 2:
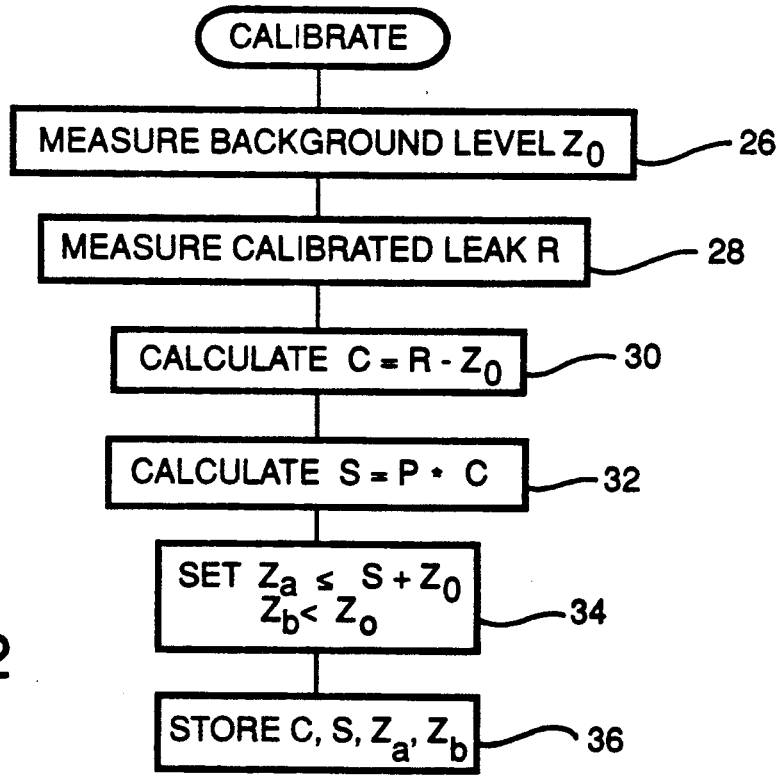
FIGS. 2-5 are flow charts illustrating the method of the invention.

Calibration of the detector 10 is initiated by pressing the calibration pushbutton 14 and measuring fresh air to establish a baseline background level $Z_o$, and then holding the probe adjacent a standard calibrated leak which represents the desired limit of allowable leaks to take a reading R. The calibration procedure is set forth in flow-chart form in FIG. 2. The background level and the calibrated leak test are accomplished in steps 26 and 28. Then in step 30 the calibrated pass/fail level C is determined as the difference of the measured values R and $Z_o$. Then in step 32 a search threshold S is calculated by multiplying the pass/fail level C by a fraction P. P is selected according to the desired sensitivity of the detector, a low threshold providing greater sensitivity. Typically, the fraction P may be on the order of 0.2. In step 34 background boundaries $Z_a$ and $Z_b$ respectively above and below $Z_o$ are selected based on the expected normal variation in the autozero level Z over a typical search period. These boundaries define an allowable range of absolute values for the autozero Z to fall between during the usage period. $Z_a$ should be less than or equal to $S+Z_o$. Thus the calibration procedure sets two relative levels, C and S, and two absolute levels $Z_a$ and $Z_b$, and in step 36 these values are stored for use during leak detection.

Figure 3:
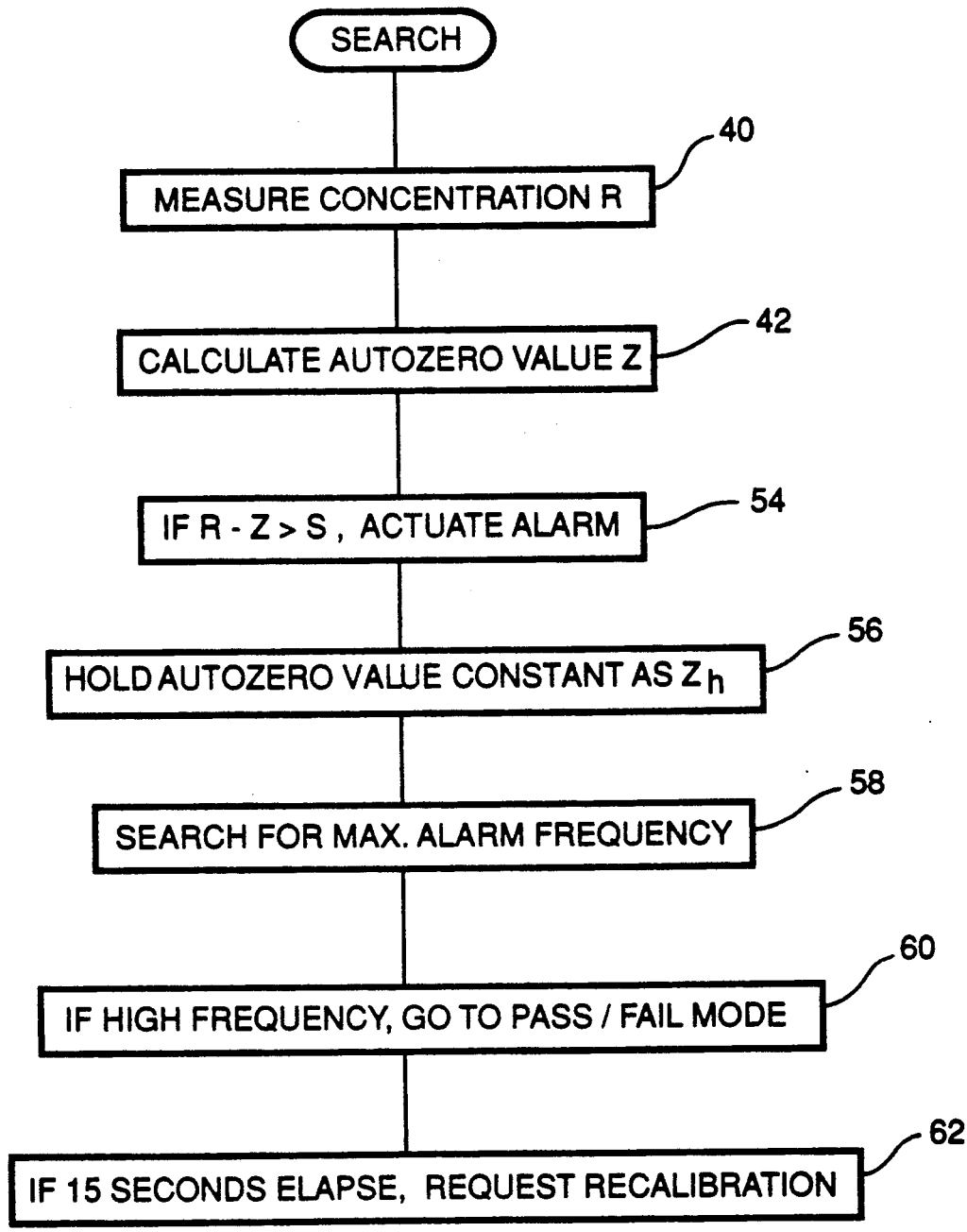
Figure 4:
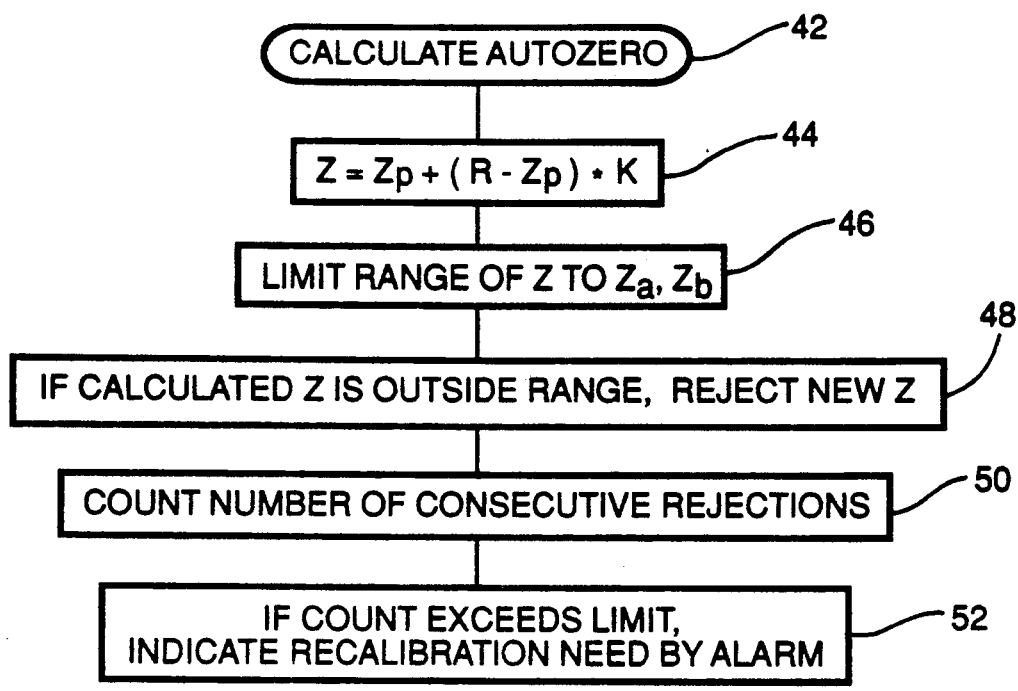

To begin a search for a leak, no buttons are pressed and the probe is moved over the product being tested at a rate of about 2 inches per second. As depicted in FIG. 3, gas concentrations readings R are taken (step 40) at least five times per second and may be taken at, say 100 times per second. The autozero value Z is constantly updated in step 42 to slowly reflect changes in the background level. A number of updating schemes are possible, such as calculating a moving average. As shown in FIG. 4, another method is to add to the previous background $Z_p$ a fraction K of the difference of the current reading R and the previous background as in step 44. Specifically, $Z=Z_p+(R-Z_p)*K$, where $K=(1-e^k)$, and $k=-SamplingInterval/TimeCounstant$. A time constant of about 10 seconds is desirable. The value K is a constant and need not be recalculated unless the time constant is changed. The value of Z is limited to the boundaries $Z_a$ and $Z_b$ (step 46). If Z attempts to go beyond either limit $Z_a$ or $Z_b$ the last update is rejected (step 48). Several consecutive rejections indicate that a significant change in background has occurred or the sensor has experienced serious drift or loss of calibration. Either event is cause for recalibration. When consecutive rejections occur they are counted (step 50) and when a preset count is reached an alarm is issued (step 52) to warn the operator of the need to recalibrate.

Returning to FIG. 3, during the search, signal levels exceeding the background are compared to the search threshold S. Thus if $R-Z$ is greater than S a leak is suspected (step 54) and the autozero value Z is held at a constant value $Z_h$ (step 56) so that the high concentrations associated with the leak do not affect the autozero. At the same time the light 20 begins to flash at a frequency related to the leak size $(R-Z_h)$ or the alarm 22 sounds with a pitch related to the leak size. Preferably the sound frequency should increase geometrically to the measured concentration so that doubling of the measured concentration results in the same increase in pitch of the output; the light 20 flashing frequency should change in the same way. By moving the probe in response to the alarm and light the operator can quickly pin-point the location of the leak (step 58). Then the pass/fail mode is invoked (step 60) by pressing the pushbutton 16. If the pass/fail mode is not selected within 15 seconds after the alarm is actuated in step 54, and the value of $R-Z$ remains above S, a recalibration is requested (step 62) since it is assumed that the operator would not hold the probe near a leak so long without switching to the pass/fail mode.

Figure 5:
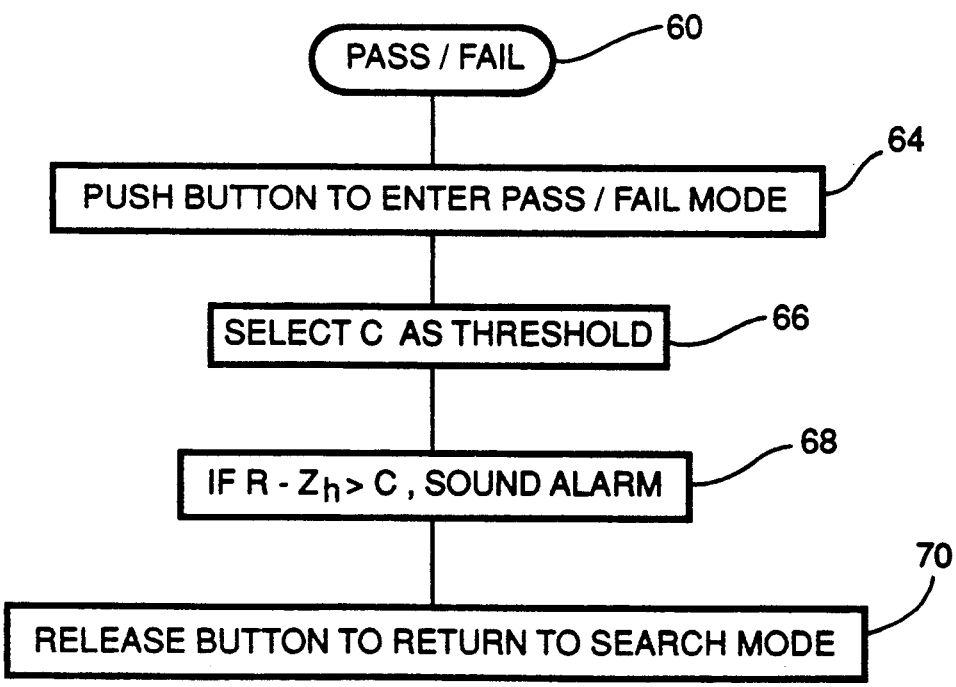

When the leak is located, it must be compared with the pass/fail level C to determine whether the leak is small enough to be ignored or large enough to require rejection or repair. As shown in FIG. 5, the operator pushes the pushbutton 16 (step 64) to cause the value C to be used as the threshold instead of S (step 66). Thus if $R-Z_h$ exceeds C the leak fails the test and the alarm 22 is sounded (step 68). Releasing the button 16 returns the process to the search mode (step 70). The autozero hold mode is maintained until the button 16 is released and the probe 12 is moved to a low concentration area. Whenever the hold mode is terminated and the autozero calculation resumes, the starting point $Z_p$ for the calculation should be the hold value $Z_h$.

If the autozero were not already in a hold mode, pushing the button 16 would effect the hold mode. This is useful for an alternative method of testing the size of the leak wherein after the leak is located, the probe is moved from the leak to draw in fresh air for a few seconds to restore the background value and then the button 16 is pushed to hold the autozero. Then the probe is returned to the leak site and the difference value $R-Z_h$ is tested against the pass/fail threshold.

The embodiments of the invention in which an exclusive property or privilege is claimed are defined as follows:

1. The method of detecting leaks using a leak detector for measuring the concentration of a test gas and having a probe, an annunciator, and a switch, comprising the steps of:

establishing a limit value of gas concentration;

establishing a threshold lower than the limit value;

moving the probe along a path and continuously measuring the gas concentration;

determining an autozero value of the concentration measurements;

subtracting the autozero value from each measurement to obtain difference values;

when the difference values exceed the threshold, holding the autozero value at a constant level and actuating the annunciator at a frequency to signal the magnitude of the difference values;

moving the probe to seek the maximum of the difference values;

exchanging the limit value for the threshold value by operating the switch; and issuing a signal when the difference value exceeds the limit value.

2. The invention as defined in claim 1 wherein the step of determining an autozero value further includes limiting the autozero value to a predetermined range of values.

3. The invention as defined in claim 1 wherein the step of determining an autozero value further includes establishing a calibration value of background gas concentration and limiting the autozero value to a predetermined range above and below the calibration value.

4. The invention as defined in claim 1 wherein the step of determining an autozero value further includes limiting the autozero value to a predetermined range of values by rejecting any concentration measurement which would cause the autozero value to go outside the range.

5. The invention as defined in claim 4 wherein the number of consecutive rejections is counted and a warning signal is given when the count reaches a set value, thereby warning of a need for detector calibration.

6. The invention as defined in claim 1 wherein the autozero value is determined by calculating a moving average of the measurements.

7. The invention as defined in claim 1 wherein the step of issuing a signal comprises comparing the difference value to the limit value and energizing the annunciator when the difference value exceeds the limit value.

8. The method of detecting leaks using a leak detector for measuring the concentration of a test gas and having a probe, an annunciator, and a switch, comprising the steps of:

establishing a limit value of gas concentration;

establishing a threshold lower than the limit value to provide increased sensitivity to low concentrations;

moving the probe along a path and continuously measuring background level and the gas concentration from leaks;

when the gas concentration exceeds the threshold, indicating changes in the concentration;

in response to the indicated changes, moving the probe to seek the maximum concentration;

when the probe is near the maximum concentration, comparing the gas concentration to the limit value; and issuing a signal when the concentration exceeds the limit value.

9. The invention as defined in claim 8 wherein the step of establishing a threshold comprises multiplying the limit value by a factor less than unity.

* * * * *